US008748178B2

(12) United States Patent
Egli et al.

(10) Patent No.: US 8,748,178 B2
(45) Date of Patent: Jun. 10, 2014

(54) METHOD FOR PRODUCING PLURIPOTENT STEM CELLS

(75) Inventors: Dietrich M. Egli, New York, NY (US); Scott A. Noggle, New York, NY (US); Kevin C. Eggan, New York, NY (US)

(73) Assignee: The New York Stem Cell Foundation, New York, NY (US)

( * ) Notice: Subject to any disclaimer, the term of this patent is extended or adjusted under 35 U.S.C. 154(b) by 0 days.

(21) Appl. No.: 13/302,109

(22) Filed: Nov. 22, 2011

(65) Prior Publication Data

US 2012/0129260 A1    May 24, 2012

Related U.S. Application Data

(60) Provisional application No. 61/416,592, filed on Nov. 23, 2010.

(51) Int. Cl.
*C12N 5/00* (2006.01)
*C12N 5/02* (2006.01)
*C12N 5/071* (2010.01)
*C12N 5/07* (2010.01)
*C12N 5/10* (2006.01)

(52) U.S. Cl.
USPC ........... 435/377; 435/375; 435/366; 435/363; 435/455

(58) Field of Classification Search
USPC ....................................................... 435/377
See application file for complete search history.

(56) References Cited

U.S. PATENT DOCUMENTS

| | | | |
|---|---|---|---|
| 2004/0146865 | A1 | 7/2004 | Robl et al. |
| 2005/0106554 | A1 | 5/2005 | Palecek et al. |
| 2007/0048864 | A2 | 3/2007 | Parikh et al. |
| 2009/0004740 | A1 | 1/2009 | Mitalipov et al. |
| 2009/0111185 | A1 | 4/2009 | Hillis et al. |

FOREIGN PATENT DOCUMENTS

| | | |
|---|---|---|
| WO | WO97/07669 | 3/1997 |
| WO | WO00/22578 | 4/2000 |

OTHER PUBLICATIONS

Xu et al., "Revealing a core signaling regulatory mechanism for pluripotent stem cell survival and self-renewal by small molecules", *Proc. Natl. Acad. Sci. USA.*, 107(18):8129-34 (2010).
Society for Assisted Reproductive Technology & the American Society for Reproductive Medicine. Assisted reproductive technology in the United States: 2001 results generated from the American Society for Reproductive Medicine/Society for Assisted Reproductive Technology registry. Fertil. Steril. 87,1253-1266 (2007).
Baguisi et al, Production of goats by somatic cell nuclear transfer, 1999, Nature Biotechnology, vol. 17, 456-461.
Braude, P., Bolton, V.& Moore, S. Humangene expression first occurs between the four- and eight-cell stages of preimplantation development. Nature 332, 459-461(1988).
Byrne et al, Producing primate embryonic stem cells by somatic cell nuclear transfer, Nov. 2007, Nature, 450:22, 497-502.
Campbell, et al., Sheep cloned by nuclear transfer from a cultured cell line, Nature, vol. 380, 64-66, Mar. 7, 1996.
Campbell, et al., Nuclear Transfer in Practice, Cloning and Stem Cells, vol. 3, No. 4, 2001, 201-208.
Chesne, et al. Cloned rabbits produced by nuclear transfer from adult somatic cells, Nature Biotechnology, Apr. 2002, vol. 20, 366-369.
Chin, M. H. et al. Induced pluripotent stem cells and embryonic stem cells are distinguished by gene expression signatures. Cell Stem Cell 5, 111-123 (2009).
Chung, Y. et al. Reprogramming of human somatic cells using human and animal oocytes. Cloning Stem Cells, vol. 11, 213-223 (Nov. 2, 2009).
Cibelli, J. et al. Somatic cell nuclear transfer in humans: pronuclear and early embryonic development. J. Regen. Med. vol. 2, 25-31 (Nov. 26, 2001).
Cowan, C. A., Atienza, J., Melton, D. A. & Eggan, K. Nuclear Reprogramming of Somatic Cells After Fusion with Human Embryonic Stem cells. Science 309,1369-1373 (2005).
Daley, G. Q. et al. Ethics. The ISSCR guidelines for human embryonic stem cell research. Science vol. 315, 603-604 (Feb. 2, 2007).
Doi, A. et al. Differential methylation of tissue- and cancer-specific CpG island shores distinguishes human induced pluripotent stem cells, embryonic stem cellsand fibroblasts. Nature Genet. 41, 1350-1353 (2009).
Draper, J. S. et al. Recurrent gain of chromosomes 17q and 12 in cultured human embryonic stem cells. Nature Biotechnol. vol. 22, 53-54 (Jan. 2004).
Egli, et al. Reprogramming within hours following nuclear transfer into mouse but not human zygotes, Nature Communications, Oct. 2011, 1-10.
Egli, et al. Impracticality of egg donor recruitment in the absence of compensation. Cell Stem Cell doi:10.1016/j. stem.2011.08.002 (in the press) 293-294.
French, A. J. et al. Development of human cloned blastocysts following somatic cell nuclear transfer with adult fibroblasts. Stem Cells 26, 485-493 (2008).
Ghosh, Z. et al. Persistent donor cell gene expression among human induced pluripotent stem cells contributes to differences with human embryonic stemcells. PLoS ONE 5, e8975 (2010).
Gore, A. et al. Somatic coding mutations in human induced pluripotent stem cells. Nature 471, 63-67 (2011).

(Continued)

*Primary Examiner* — Valarie Bertoglio
(74) *Attorney, Agent, or Firm* — DLA Piper LLP (US)

(57) ABSTRACT

Methods are provided for producing a human embryo capable of developing to the blastocyst stage. The method includes transferring a human somatic cell genome into a mature human oocyte by nuclear transfer and activating the oocyte, without removing the oocyte genome. Pluripotent human embryonic stem cells, and methods of obtaining these, are also provided.

4 Claims, 12 Drawing Sheets

(56) References Cited

OTHER PUBLICATIONS

Hall, V. J. et al. Developmental competence of human in vitro aged oocytes as host cells for nuclear transfer. Hum. Reprod. 22, 52-62 (2007).

Heindryckx, B., De Sutter, P., Gerris, J., Dhont, M. & Van der Elst, J. Embryo development after successful somatic cell nuclear transfer to in vitro matured human germinal vesicle oocytes. Hum. Reprod. 22, 1982-1990 (2007).

Hu, B. Y. et al. Neural differentiation of human induced pluripotent stem cells follows developmental principles but with variable potency. Proc. Natl Acad. Sci. USA 107, 4335-4340 (2010).

Hussein, S. M. et al. Copy number variation and selection during reprogramming to pluripotency. Nature 471, 58-62 (2011).

Kennedy, D. Editorial retraction. Science 311, 335 (2006).

Kim, K. et al. Epigenetic memory in induced pluripotent stem cells. Nature 467, 285-290 (2010).

Klitzman, R.& Sauer, M. V. Payment of egg donors in stemcell research in the USA. Reprod. Biomed. Online 18, 603-608 (2009).

Lister, R. et al.Hotspots of aberrant epigenomic reprogramming in human induced pluripotent stem cells. Nature 471, 68-73 (2011).

Mayshar, Y. et al. Identification and classification of chromosomal aberrations in human induced pluripotent stem cells. Cell Stem Cell 7, 521-531 (2010).

McElroy et al. Developmental competence of immature and failed/abnormally fertilized human oocytes in nuclear transfer. Reprod. Biomed. Online 16, 684-693 (2008).

Medicine, The Ethics Committee of the American Society for Reproductive Medicine. Financial compensation of oocyte donors. Fertil. Steril. 88, 305-309 (2007).

Mitalipov, S. M. et al. Reprogramming following somatic cell nuclear transfer in primates is dependent upon nuclear remodeling. Hum. Reprod. 22, 2232-2242 (2007).

Polejaeva, Irina A. et al. Cloned pigs produced by nuclear transfer from adult somatic cells, Nature, vol. 407, Sep. 7, 2000.

Revazova, E. S. et al. Patient-specific stem cell lines derived from human parthenogenetic blastocysts. Cloning Stem Cells 9, 432-449 (2007).

Rideout, William M., et al. Correction of a Genetic Defect by Nuclear Transplantation and Combined Cell and Gene Therapy, Cell, vol. 109, 17-27, Apr. 5, 2002.

Stojkovic, M. et al. Derivation of a human blastocyst after heterologous nuclear transfer to donated oocytes. Reprod. Biomed. Online 11, 226-231 (2005).

Takahashi, K. et al. Induction of pluripotent stem cells from adult human fibroblasts by defined factors. Cell 131, 861-872 (2007).

Thomson, J. A. et al. Embryonic stem cell lines derived from human blastocysts. Science 282, 1145-1147 (1998).

Wakayama et al., Full-term development of mice from enucleated oocytes injected with cumulas cell nuclei, Nature 394, 369-374; Jul. 23, 1998.

Wells et al., Production of Cloned Calves Following Nuclear Transfer with Cultured Adult Mural Granulosa Cells, Biol. Reprod. 60, 996-1005), 1999.

Wilmut et al., Viable offspring derived from fetal and adult mammalian cells, Nature 385, 810-813; Feb. 27, 1997.

Zhang, K. et al. Digital RNA allelotyping reveals tissue-specific and allele-specific gene expression in human. Nature Methods 6, 613-618 (2009).

Dimos, et al. Induced Pluripotent Stem Cells Generated from Patients with ALS Can Be Differentiated into Motor Neurons. Science 321, 1218-1221 (2008).

Noggle, et al. Human oocytes reprogram somatic cells to a pluripotent state, Nature vol. 478: 70-76, Oct. 6, 2011.

Chen, et al. Optimal Timing of Inner Cell Mass Isolation Increases the Efficiency of Human Embryonic Stem Cell Derivation and Allows Generation of Sibling Cell Lines, Cell Stem Cell 4, 103-106 (2009).

Freberg, et al. Epigenetic Reprogramming of OCT4 and NANOG Regulatory Regions by Embryonal Carcinoma Cell Extract, Mol. Biol. Cell 18, 1543-1553 (2007).

Imamura, et al. Transcriptional repression and DNA hypermethylation of a small set of ES cell marker genes in male germline stem cells. BMC Developmental Biology 6:34 (2006).

Pick, et al. Clone- and Gene-Specific Aberrations of Parental Imprinting in Human Induced Pluripotent Stem Cells. Stem Cells 27, 2686-2690 (2009).

spindle out-in parthenote

Developmental progression 'Transfer only'

Karyotype soPS2 mitochondrial genotype

Expression of pluripotency markers

Differentiation into three germ layers

Cluster diagram of global gene expression

DNA methylation analysis expression of somatic alleles

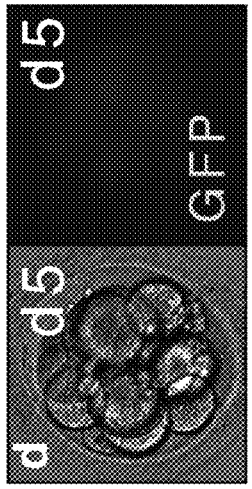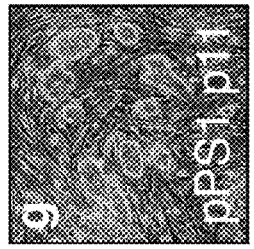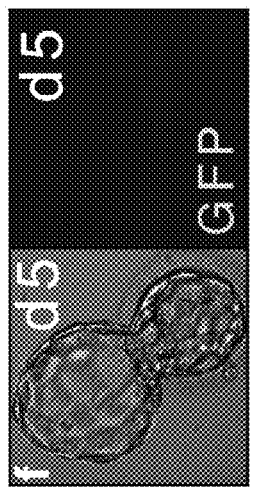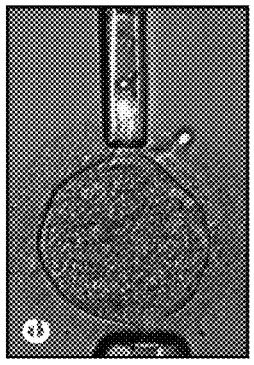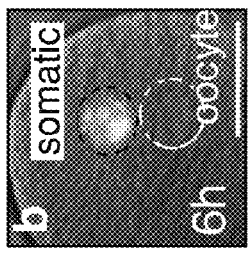
FIG. 6b  FIG. 6c  FIG. 6d  FIG. 6e  FIG. 6f  FIG. 6g Karyotype 46 XX

METHOD FOR PRODUCING PLURIPOTENT STEM CELLS

CROSS-REFERENCE TO RELATED APPLICATIONS

This application claims the benefit of U.S. Provisional Patent Application No. 61/416,592, filed on Nov. 23, 2010, the disclosure of which is incorporated by reference in its entirety.

FIELD OF THE INVENTION

The invention is broadly directed to methods for producing stem cells. More specifically, the invention is directed to a method for producing human blastocysts by transferring a human somatic cell genome into a mature oocyte by nuclear transfer without removing the oocyte genome.

BACKGROUND OF THE INVENTION

The cloning of frogs from somatic cells demonstrated that differentiation from the zygote into specialized cell types was a reversible process. The transplantation of somatic nuclei into unfertilized mammalian oocytes resulted in the cloning of sheep, mice, cows and various other mammalian species.

The derivation of embryonic stem cells from human blastocysts brought the prospect of combining nuclear transfer and stem cell derivation to generate cells and tissues for patients requiring replacement of diseased cells or tissue. This concept was realized in the mouse for the correction of immunodeficiency and of Parkinson's disease (Rideout et al. 2002 *Cell* 109(1): 17-27). Nuclear transfer stem cells were also derived from the rhesus monkey (Byrne et al., 2007 *Nature* 450 (7169): 497-502). However, these techniques have previously not been accomplished in human cells, possibly because of species-specific differences.

To date, no methods are known for the derivation of a human embryonic stem cell line after nuclear transfer, although nuclear transfer embryos have been generated which have developed to the cleavage stages. Human embryos generated by conventional nuclear transfer methods consistently arrest at the late cleavage stages with karyotypic and transcriptional defects, prohibiting stem cell derivation. Thus, there remains a longstanding need in the art for a method for the nuclear transfer of human cells, combined with the derivation of embryonic stem cells.

SUMMARY OF THE INVENTION

It has now been found that human oocytes can reprogram a somatic cell genome to an embryonic state. When the oocyte genome is not removed, nuclear transfer embryos frequently develop to the blastocyst stage. Embryonic stem cells derived from these blastocysts are pluripotent and contain a diploid somatic cell genome reprogrammed to an embryonic state.

A human somatic cell genome is transferred into a mature MII oocyte. The oocyte is activated and the embryo is allowed to develop to the blastocyst stage, resulting in an embryo that contains both the somatic cell genome as well as a haploid oocyte genome.

After six to seven days of development, or once the embryo has reached the expanded blastocyst stage, the inner cell mass of the embryo is isolated. Stem cells are generated from this inner cell mass. Analysis of gene expression and developmental potential is performed to demonstrate pluripotency and karyotype and short tandem repeat analysis is performed to show the presence of the somatic cell genome in the stem cell line. The results show that the human oocyte reprogrammed a somatic cell genome to an embryonic state.

In particular, one embodiment, the invention provides a method for producing a human nuclear transfer embryo capable of developing into a blastocyst, the method comprising:

transferring a human somatic cell genome into a mature human oocyte by nuclear transfer and activating the oocyte, wherein the method is, in a further particular embodiment, conducted without removing the human oocyte genome.

The invention further provides methods for allowing the human nuclear transfer embryo to develop to a blastocyst.

The invention also provides a method for preparing pluripotent stem cells comprising the steps of: isolating an inner cell mass from a human nuclear transfer embryo at the blastocyst blastocyst stage and generating from the cell mass a pluripotent embryonic stem cell line, comprising a genome derived from the somatic cell.

The invention also optionally provides that the generating step is conducted by contacting the inner cell mass with a human embryonic stem cell medium that comprises Rho kinase inhibitors Y27632 and thiazovivin, for a period of time until an outgrowth of pluripotent stem cells is observed. The period of time ranges from 3 to 10 days and more typically is 4 days.

In a further embodiment of the invention, pluripotent stem cells are prepared by a method comprising the steps of:

ablating the trophectoderm of the blastocyst of claim 3 with laser pulses, plating an inner cell mass of the blastocyst on a fibroblast feeder layer in human embryonic stem cell media supplemented with thiazovivin and Rock inhibitor, ablating remaining non-inner cell mass cells with laser pulses as needed, obtaining an outgrowth of cells, from the plated inner cell mass, expanding the outgrowth into a cell line that can be cryopreserved and thawed, and perpetually passaged.

In a further embodiment of the invention, the pluripotent stem cell comprises a genome derived from the human somatic cell and a haploid genome derived from the human oocyte. Alternatively, the pluripotent stem cell comprises a diploid genome derived from the human oocyte.

In a further embodiment, the invention provides a differentiated cell generated from the pluripotent stem cells of the invention. The differentiated cell is, for example, selected from one or more of the following: an insulin producing cell, a neuron, a liver cell, a heart cell, a bone cell, a gut cell, a skin cell, a hormone producing cell and/or a blood cell.

It will be appreciated by the artisan that a human pluripotent stem cell obtained by the inventive method does not constitute a "human organism."

BRIEF DESCRIPTION OF THE DRAWINGS

FIG. 1a is a schematic of nuclear transfer into human oocytes. The oocyte genome is removed and replaced with a diploid but unreplicated somatic cell genome. The somatic genome undergoes chromosome condensation. Upon activation, the egg exits meiosis and initiates development.

FIG. 1b depicts the human oocyte using the Oosight™ system before removal of the genome.

FIG. 1c depicts the donor cell population marked with either H2B:GFP or GFP.

FIG. 1*d* depicts a somatic chromatin three hours after transfer into the oocyte.

FIG. 1*e* depicts the time point at which chromosome condensation has occurred.

FIG. 1*f* depicts the developmental potential of donor eggs after in vitro fertilization ("IVF"), parthenogenesis or nuclear transfer (termed here genome-exchange) with either a somatic cell nucleus or a blastomere nucleus. The time points that a particular developmental stage is reached is indicated in days. ZGA=zygotic genome activation.

FIG. 1*g* depicts an arrested nuclear transfer embryo, with somatic cells used as donor nuclei.

FIG. 1*h* depicts a parthenote after removal and reinsertion of the genome. These develop.

FIG. 2*a* is a schematic of nuclear transfer without removal of the oocyte genome, or, controls with removal of the oocyte or the somatic cell genome at the first interphase.

FIG. 2*b* depicts the development of embryos from the first mitosis to the blastocyst stage, containing the diploid somatic genome as well as the haploid oocyte genome.

FIG. 2*c* depicts the developmental potential of embryos and controls. The time points where a particular developmental stage is reached are indicated in days. ZGA indicates zygotic genome activation.

FIG. 3*a* depicts the triploid karyotype.

FIG. 3*b* depicts the mitochondrial DNA analysis of hypervariable region I.

FIG. 3*c* depicts the expression of pluripotency markers.

FIG. 3*d* depicts immunostaining and tissue structures of differentiated cells, including neurons, muscle cells, and cells of the endoderm lineage.

FIG. 3*e* depicts a cluster diagram of gene expression.

FIG. 4*a* depicts the bisulfite sequencing of the promoters of the nanog gene that is methylated to a higher extent in skin cells than in stem cells. Closed circles represent methylated cytosines, open circles represent unmethylated cytosines.

FIG. 4*b* shows the DNA sequences from cDNA of nanog and Oct4. It demonstrates that nanog and Oct4 is expressed from the reprogrammed somatic genome. Nanog and Oct4 are not expressed in skin cells.

FIGS. 6*a*-6*g* depict a method for generating a parthenogenetic stem cell line. They also show a method to distinguish between oocyte and somatic cell genome upon transfer. By marking the skin cell genome with a fluorescent protein, it can be distinguished from the oocyte genome after transfer. Fluorescence remains associated with the somatic genome, but not with the oocyte genome.

FIG. 6*a* depicts a method to generate parthenogenetic embryos that can give rise to a stem cell line (and nuclear transfer embryos that do not).

FIG. 6*b* shows an embryo with the transferred somatic genome and the oocyte genome that had not been removed, at the first interphase.

FIG. 6*c* shows the removal of the oocyte genome.

FIG. 6*d* shows an arrested nuclear transfer embryo,

FIG. 6*e* depicts the removal of the somatic cell genome.

FIG. 6*f* depicts the parthenogenetic embryo at the blastocyst stage.

FIG. 6*g* depicts an embryonic stem cell line derived from this parthenogenetic embryo.

FIG. 7*a* depicts the expression of pluripotency markers of a parthenogenic cell line.

FIG. 7*b* depicts immunostaining of differentiated cells, including neurons, muscle cells, and cells of the endoderm lineage of a parthenogenic cell line.

FIG. 7*c* depicts the differentiation of parthenogenetic stem cells into tissues of all three germ layers as teratomas.

FIG. 7*d* is the karyotype of the parthenogenetic stem cell.

DETAILED DESCRIPTION OF THE INVENTION

Figure 1A:
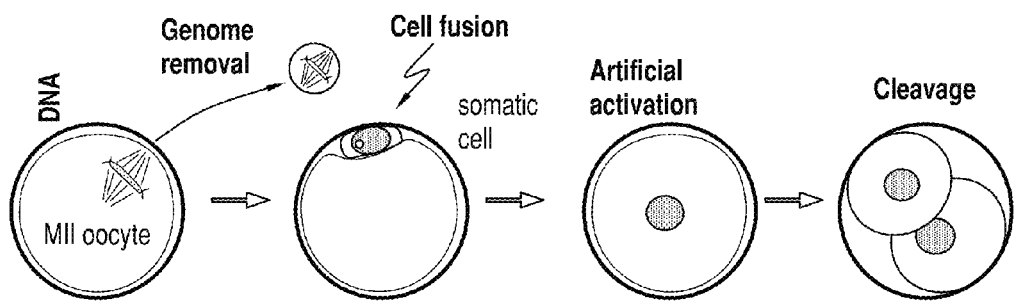
FIGS. 1a-1h depict developmental defects resulting after standard nuclear transfer.

Accordingly, it has now been found that nuclear transfer of the nucleus of a differentiated adult cell into a human oocyte that retains the haploid oocyte genome, i.e., the oocyte genome is not extracted, produces an oocyte that is capable of being activated and of developing up to and past the blastocyst stage of development. Heretofore, human oocytes that have been subjected to more conventional nuclear transfer methods, where the oocyte nucleus has been extracted as part of the nuclear transfer process, have been reported to be incapable of developing to the blastocyst stage. Without meaning to be bound by any theory or hypothesis as to the operation of the invention, it seems that the haploid oocyte genome rescues the development process after nuclear transfer and permits an embryo to develop past the stage at which conventional human nucleatransfer embryos stopped developing, albeit with a triploid genome.

As used herein, the term "adult" means post-fetal, i.e., a differentiated adult cell is from an organism from the neonate stage through the end of life, unless otherwise specified.

As used herein, the term "pluripotent stem cell" or PS is intended to apply to cells capable of differentiating into tissues of all three germ or dermal layers: mesoderm, endoderm, and ectoderm, unless otherwise specified.

As used herein, the term "embryo" applies to an activated oocyte that has divided to the two cell stage or beyond, e.g., to the four, eight, sixteen and higher stages of developments, unless otherwise specified.

As used herein, the phrase, "nuclear transfer human embryo" refers to an embryo produced by the inventive methods, e.g., by inserting the genome derived from an adult human cell into a human oocyte, with or without removal of the haploid oocyte genome. A "nuclear transfer human embryo" according to the invention is distinguished from a conventionally produced human embryo, i.e., distinct from an embryo produced by the penetration of an ovum by a male sperm cell that is typically capable of fully developing into a human being.

The work described herein was also reported by Noggle et al., 2011 *Nature* 478:70-76, the contents of which are incorporated by reference herein.

Nuclear Transfer Techniques

The techniques of nuclear transfer are well known and were developed for the cloning of several animal species, in particular of mammals, such as the sheep (Wilmut et al., 1997 *Nature* 385, 810-813; WO 97 07669), the mouse (Wakayama et al., 1998 *Nature* 394, 369-374; WO 99 37143), cattle (Wells et al., 1999 *Biol. Reprod.* 60, 996-1005), the goat (Baguisi et al., 1999 *Nature Biotechnol.* 17, 456-461; WO 00 25578), the pig (Polejaeva et al., 2000 *Nature* 407, 86-90) and the rabbit (Chesne et al., 2002 *Nature Biotechnol.* 20, 366-369). The methods of nuclear transfer are described in particular by Campbell et al. (Nuclear transfer in practice, School of Biosciences, University of Nottingham, Leicestershire, United Kingdom).

In brief, the insertion of a donor cell or nucleus into an oocyte to form a reconstituted cell is usually accomplished by microinjection of a donor cell under the zona pellucida prior to fusion. As noted supra, the art has heretofore conducted nuclear transfer after extracting the oocyte nucleus. Fusion of the inserted cell or nucleus may be induced by application of a DC electrical pulse across the contact/fusion plane (electrofusion), by exposure of the cells to fusion-promoting chemicals, such as polyethylene glycol, or by way of an inactivated virus, such as the Sendai virus.

A reconstituted cell is typically activated by electrical and/or non-electrical means before, during, and/or after fusion of the nuclear donor and recipient oocyte. Activation methods broadly include the application of electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in media well known to those of ordinary skill in the art.

It is contemplated that the methods of the invention can be conducted wherein nuclear transfer and artificial activation may be performed in that order, or in any other order, such as with nuclear transfer first, activation second or in the reverse order.

Ooeyte Culture and Manipulation

The methods of the invention require that the oocyte, donor cells and resulting embryos be cultured or manipulated in physiologically suitable media.

The oocytes were transported from the IVF laboratory to the site of manipulation in a portable incubator (INC-RB1, CryoLogic) heated to 37° C. in GMOPSplus media available from Vitrolife. The oocytes were manipulated in GMOPSplus media. The oocyte were maintained and cultured in Global media available from IVFOnline, LLC. In general, all manipulations were performed in media that maintain a physiological environment at ambient atmosphere, while all culture is done in media that maintain a physiological environment at 5% CO2. All media were supplemented with a source of protein, e.g., human serum albumin or plasma without active complement factors (plasmanate). Plasmanate, available from Talecris, was added to Global media at 10% volume percentage. Other media that may be employed for manipulating the oocyte include: HTF (IVFOnline, LLC or other supplier), Ham's F-10 or a modified version of it (Irvine Scientific), Gamete Buffer (Cook medical), or other media that maintain physiological conditions at ambient atmosphere. Maintenance and culture of oocytes, activated oocytes and embryos until day 7 post activation can also be performed in other commercially available ART media (Life-Global or IVFOnline, LLC). These media are either single-step media that can be used from day 1 to day 7, such as Global media, or the Single Step Medium from Irvine Scientific, or they are two-step media, that require a change on day 3 after activation, such as Cook cleavage medium (from Cook Medical, Inc.) for day 1 to day 3 followed by Cook Blastocyst medium (from Cook Medical, Inc.) until day 7 post activation. Other examples for 2-step media are P-1 medium and the MultiBlast Medium (from Irvine Scientific), or the Quinn's Advantage Cleavage media and the Quinn's Advantage Blastocyst media (Cooper Surgical). Embryos are cultured in small drops of 30-50 microliter media, covered with oil. Oil can be obtained from Irvine Scientific under the name "oil for embryo culture," from Cook Medical under the name "culture oil," from IVFOnline, LLC under the name "LiteOil," or from another vendor. Embryos can also be cultured in small dishes or wells, such as 4-well cell culture plates from Thermo Scientific, containing 500 to 700 microliter of medium that do not need to be covered with oil because of the larger volume.

Micromanipulation was performed using pipets purchased from Origio, brand of the needles Humagen, from Cook Medical or from Eppendorf, or another vendor of micromanipulation pipettes. All pipets can also be laboratory-made using a needle puller and a microforge. The micromanipulator can be from Narishige, Sutter Instruments, Eppendorf or another manufacturer of micromanipulators. The microscope used for manipulations was an inverted microscope with a heated stage and equipped with the said micromanipulator. The microscope can be a NikonTE2000-U equipped with a 40× objective and Hoffman contrast optics, or an Olympus IX71 with relief contrast optics, or an equivalent microscope from another manufacturer.

Somatic Cell Introduction

Somatic cells were introduced into the oocytes by an 20 µs 1.3 kV/cm electrical pulse in cell fusion medium 0.26M mannitol, 0.1 mM MgSO4, 0.05% BSA, 0.5 mM 4-(2-hydroxyethyl)-1-piperazineethanesulfonic acid ("HEPES"). Under these conditions, the electrical pulse was sufficient to induce reliable fusion within 5-20 minutes, while preventing oocyte lysis and preventing spontaneous activation. Stronger electrical pulses frequently result in oocyte lysis. Calcium was avoided in the medium to prevent spontaneous activation. The electrical pulse was delivered with an Electro Cell Fusion Generator, LF201, (Nepagene). The electrical pulse could also be made with a different fusion medium, as long as optimizations are made to both prevent oocyte lysis and prevent spontaneous activation of the oocyte. Cell introduction can also be done by direct injection or by inactivated Sendai virus, or another agent that efficiently induces cell fusion. The electrical pulse could also be delivered with another cell fusion apparatus, such as the apparatus of BTX (Harvard apparatus), as long as the conditions are optimized Derivation of Pluripotent Stem Cells The derivation of pluripotent stem cells was performed by isolation of the inner cell mass from a blastocyst with a laser. Derivation may also be performed at an earlier stage, such as from a blastomere. The derivation may also be done without the isolation of the inner cell mass, by simply plating the intact blastocyst in a dish, an approach that is less efficient than after isolation.

The inner cell mass is plated on a mouse embryonic fibroblast feeder layer. The feeder layer may also be composed of human cells, or any other suitable substrate that can support the growth of human pluripotent stem cells. Such substrates include Matrigel, UV/ozone treated plasticware, gelatin-coated plastic, or other substrate. The culture medium is composed of Knockout DMEM, 20% Knockout Serum Replacement, nonessential amino acids, 2.5% FBS, Glutamax, beta-mercaptoethanol, 10 ng/microliter bFGF, and antibiotic. The employed medium may also be a variation of this medium, e.g. without the 2.5% FBS, or with a higher or lower % of knockout serum replacement, or without antibiotic. The employed medium may also be another suitable medium that supports the growth of human pluripotent stem cells in undifferentiated conditions, such as mTeSR (available from STEMCELL Technologies), or Nutristem (available from Stemgent), or ES medium with vitronectin coated surfaces, or another equivalent medium.

The invention is further described in the following nonlimiting Examples.

Example 1

Nuclear Transfer

Two methods were developed for nuclear transfer.

For all methods, the somatic cells were allowed to grow to confluence to induce growth arrest, optionally followed by 1 day of incubation in medium with low serum content (0.5% fetal bovine serum). Prior to transfer, somatic cells were lifted from the dish using trypsin (Invitrogen), pelletted by centrifugation (1000 g for 4 min), resuspended in fibroblast medium (Dulbecco's Modified Eagle Medium ["DMEM"] plus 10% FBS, Invitrogen) and kept on ice until transfer. The oocytes were retrieved from healthy young donors (22-33 years of age). The somatic cell was introduced into the oocyte by an 20 µs 1.3 kV/cm electrical pulse in cell fusion medium 0.26M mannitol, 0.1 mM MgSO4, 0.05% BSA, 0.5 mM 4-(2-hydroxyethyl)-1-piperazineethanesulfonic acid ("HEPES"). The electrical pulse was delivered with an Electro Cell Fusion Generator, LF201, (Nepagene). The same type of pulse was used to transfer an oocyte genome or a blastomere genome.

For all micro-manipulations, the Nikon 40× ELWD Plan-Fluor 0.6 with Hoffmann modulation contrast optics was used. Manipulations were performed on a Nikon TE2000-U, equipped with a Narishige micromanipulator and a Tokai hit heating plate heated to 37° C. Glass bottom dishes (WillCo), or the lid of a petri dish with small droplets of about 30 µl covered with mineral oil (Irvine Scientific) were used for micromanipulation.

Example 2

Artificial Activation

At 3-4 hours post nuclear transfer, when chromosome condensation of the somatic cell has occurred, the oocyte was activated in 5 µM ionomycin followed by 4-6 hours in 2 mM 6-dimethylaminopurine ("6-DMAP"). The ionomycin was diluted in GMOPSplus containing HSA (Vitrolife). Embryos were then allowed to develop in embryo culture media at 5% oxygen, 6% CO2 and 89% N2, in. Global media supplemented with 10% plasmanate, in a Cook benchtop incubator. Embryo culture could also be done under ambient oxygen concentrations, and using different commercial embryo culture media, or a different incubator.

Example 3

Genome Removal

Three methods have been developed for the removal of a genome from the oocyte.

In one such method, the oocyte genome was identified at the metaphase II stage with spindle birefringence using the Oosight™ system (CRi) and then removed in the presence of 5-10 µg/ml cytochalasinB using a fire-polished pipette (as the one in FIG. 6c). The pipette was prepared in our laboratory using a Sutter needle puller and a micro-forge (Sutter instruments). In approx. a third of the nuclear transfer experiments, genome removal was done in this manner.

In another method, the location of the oocyte genome was identified at the metaphase II stage by staining in 2 µg/ml of Hoechst 33342 and minimal UV illumination and then removed in the presence of 5-10 µg/ml cytochalasinB. Minimal UV illumination is the lowest illumination that still allows the visualization of the chromosomes by eye in a dark room and after the eyes are adapted to darkness. Minimal UV illumination is achieved by closing the filters NDB, ND4, A and F on the Nikon TE2000-U. A Lambda SC Smart Shutter controller (Sutter instruments) is used to minimize the time of UV exposure. In another third of nuclear transfer experiments genome removal was performed in this way.

In a third method, the oocyte genome was removed after artificial activation when an interphase nucleus had formed. This method was used to generate the parthenogenetic stem cells.

This method did not require specialized equipment or the use of a DNA staining dye. It was done in the presence of 5-10 µg/ml cytochalasinB and 40-50 µg/ml nocodazole using a fire-polished pipette. Removal was done at least 6, or as many as 12 hours post activation. The nucleus of the oocyte and the nucleus of the somatic cell could be distinguished by GFP fluorescence: the somatic cell genome was marked with H2B-GFP transgene prior to transfer. The somatic cell genome did carry most of the green fluorescence, while the oocyte genome did not. This allowed specific removal of either genome (FIGS. 6c, 6e).

For all micro-manipulations, the Nikon 40× ELWD Plan-Fluor 0.6 with Hoffmann modulation contrast optics was used. Manipulations were performed on a Nikon TE2000-U, equipped with a Narishige micromanipulator and a Tokai hit heating plate heated to 37° C. Glass bottom dishes (WiliCo), or the lid of a petri dish with small droplets of about 30 µl covered with mineral oil (Irvine Scientific) were used for micromanipulation.

Example 4

Derivation of Stem Cell Lines

For stem cell derivation, cells were allowed to develop to the blastocyst stage, or until day 6 or day 7 after egg retrieval. Isolation of the inner cell mass was best done when the blastocysts are expanded or hatched, which usually occur late on day 6 or early on day 7 after activation. The trophectoderm was ablated with 30-50 laser pulses, each 500-700 µs wide (Chen et al. 2009 *Cell Stem Cell* 4(2): 103-106). The laser used was a Hamilton Thorne Laser system with a 40× lens. Staccato mode may also be used to ablate the trophectoderm. It was noted that single pulses give a better control. Pulses were delivered within a short time frame because the trophectoderm collapses and the inner cell mass ("ICM") may become invisible. The dead trophectoderm was then broken up by gentle pipetting through a glass capillary, or by microdissection using piezo pulses. This step was optional, blastocysts may also simply be plated upon laser application.

The inner cell mass was then plated on a fibroblast feeder layer in human embryonic stem cell media. The embryonic stem cell media contains 90-100 ml KO-SR, 500 ml knockout DMEM ("KO-DMEM"), 6.5 ml Glutamax, 6.5 ml non-essential amino acids, and 6.5 ml penicillin plus streptomycin, and 0.65 ml beta-mercaptoethanol (1000×) (all purchased from Invitrogen or other supplier). In addition, medium was supplemented with 2 µM thiazovivin (from Stemgent or other vendor) and 10 µM Rock inhibitor (EMD chemicals), as well as 2.5% FBS, and 10 ng/ml bFGF. Upon attachment, non-ICM cells were again ablated with the laser using the staccato mode (Hamilton Thorne Laser system). ICM cells were of a morphology of ES cells, small and tighly packed, while non-ICM cells were larger and generally more flat. These flat cells would inhibit the growth of the ICM cells and were ablated 1-3 times between day 3 and day 7 after plating to allow optimal outgrowth. After 4 days to 3 weeks, an outgrowth was observed for most blastocysts with an ICM. 1-2 weeks after the initial outgrowth was observed, the outgrowth was picked and expanded into a cell line that can be cryopreserved and thawed, perpetually passaged and differentiated into cell types and tissues of all germ layers.

Thiazovivin (Stemgent cat. #04-0017) and Rock inhibitor Y27632 (Stemgent Cat. #04-0012), and the ablation of non-ICM cells after plating were noted to increase the chance of a successful derivation.

Example 5

Development and Reprogramming Using Conventional Nuclear Transfer Methods

Most nuclear transfer protocols involve the removal of the oocyte genome at MetaphaseII of meiosis and the replacement with a somatic cell at interphase (FIG. 1a). Transfer was followed by chromosome condensation, thereby synchronizing the cell cycle of oocyte and somatic cell. The oocyte was then given an artificial activation stimulus to exit meiosis and initiate development as described by Example 3, above. Activation can be initiated at any reasonable time, e.g., from 2-6 hours, after transfer, but is preferably done at 3 hours post nuclear transfer, when chromosome condensation of the somatic cell has occurred. Activation agents include any art known agents, e.g., ionomycin followed by 4-6 hours in 2 mM 6-dimethylaminopurine ("6-DMAP") or 10 µM puromycin. Other calcium ionophores, such as A23187, or other protein translation inhibititors, such as cycloheximide are optionally employed as activating agents. The experiments were conducted using donor adult differentiated cells labeled with a green fluorescent protein ("GFP") or H2B:GFP (where H2B is histone H2B) fusion transgene under the control of a ubiquitously expressed promoter (FIG. 1c).

Figure 1B:
Figure 1C:
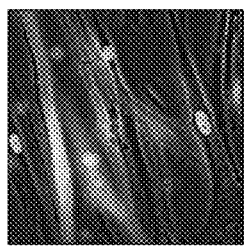
Figure 1D:
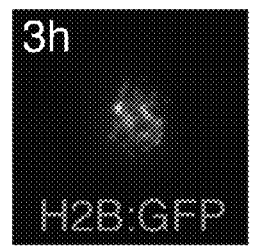
Figure 1E:
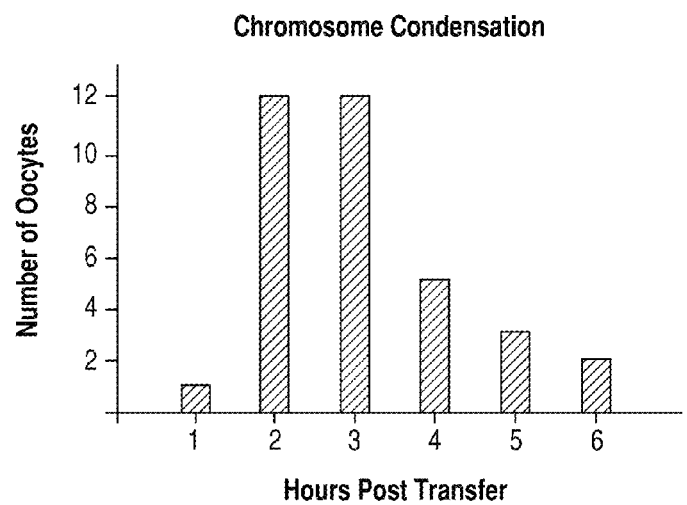
Figure 1F:
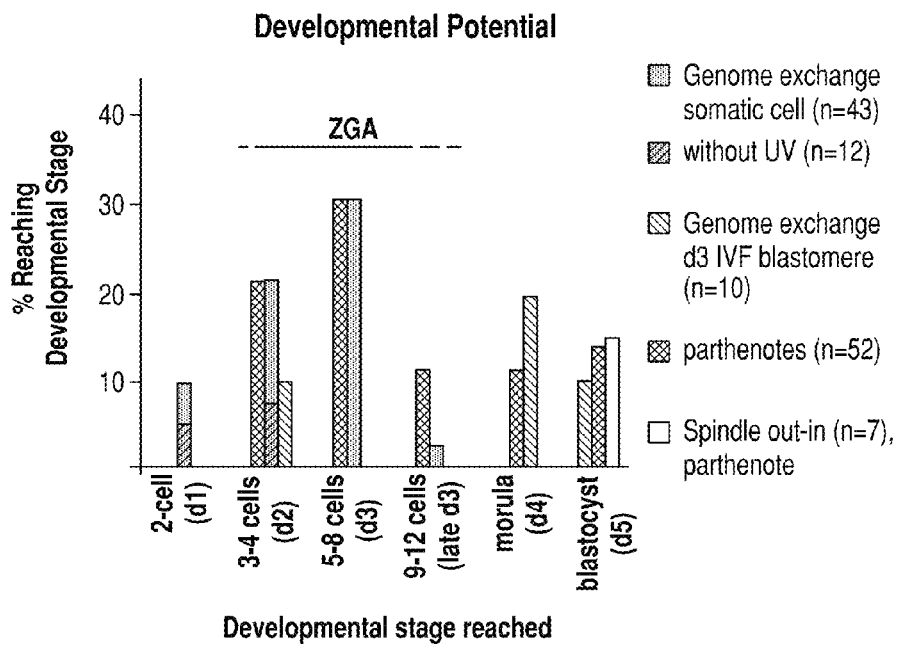

The oocyte genome was removed after visualization by microtubule birefringence (FIG. 1b). Chromosome condensation of the transferred somatic cell genome occurred efficiently in most oocytes within 2-3 hours (FIGS. 1d, 1e). Upon activation, embryos developed to the cleavage stages, but these conventional nuclear transfer embryos did not develop beyond 8-12 cells, a cell number reached on day 3 of development (FIGS. 1f, 1g).

As a control for the quality of the oocytes and the activation stimulus, IVF embryos as well as parthenogenetic embryos were used. The development to the blastocyst stage, in IVF embryos, after in vitro fertilization, was very efficient. Parthenogenetic embryos regularly developed to the morula and blastocyst stages, well beyond the developmental block seen in nuclear transfer embryos (FIG. 1f), thus confirming the quality of the oocytes and the activation stimulus.

As a control for the physical manipulations of the oocyte, the genome of oocytes were removed and re-inserted, followed by artificial activation. This allowed development to the blastocysts stage. It demonstrated that the employed manipulations were compatible with preimplantation development (FIG. 1h).

Figure 1G:
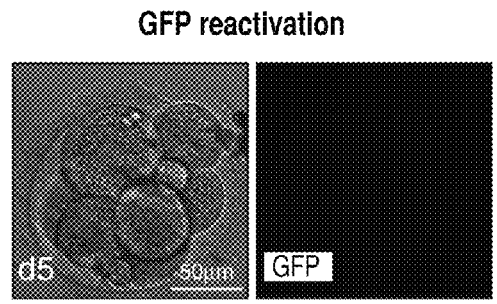
Figure 1H:
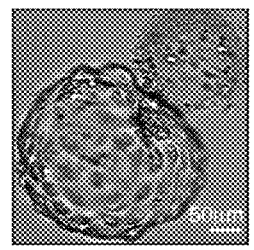

In the developmentally most advanced nuclear transfer embryos, GFP expression was undetectable, indicating that the transgene present in donor cells was not expressed (FIG. 1g).

To determine whether the developmental arrest and the lack of GFP transgene expression reflected a more general transcriptional failure, the transcriptome of nuclear transfer embryos was compared with IVF embryos, oocytes and parthenogenetic embryos. To distinguish between expression from the transferred genome and maternal contributions to transcript abundance, the data was compared to those obtained from embryos whose gene expression has been inhibited by development (from day 1) in the presence of the RNA polymerase II inhibitor alpha amanitin. It was found that transcript types and abundances in nuclear transfer embryos most closely resembled those in embryos whose transcriptional activity had been inhibited.

Genes that were up- or down-regulated between the unfertilized oocyte were then compared with IVF embryos collected late on day 3 and early day 4 of development. It was found that 761 genes upregulated, reflecting zygotic genome activation (ZGA) i.e, when transcription is activated in a normal embryo. The number of differentially regulated genes was then determined in the following additional samples: To distinguish between new transcription and differential mRNA degradation, the data was compared to embryos that were incubated in alpha amanitin from day 1 to late on day 3 or early on day 5 of development. It was found that of the 761 genes, the amanitin treated samples had, on average, 62 genes upregulated (p=0.01). Nuclear transfer embryos had on average only 124 genes upregulated (p=0.01).

The failure to properly transcribe the embryonic genome was not due to an inability to reach the stage of zygotic genome activation, as even the most advanced nuclear transfer embryos with 10-12 cells showed these transcriptional defects. This suggests that even though transcription from the transferred genome can occur, it is severely defective and insufficient to support embryonic development.

In summary, this Example confirms that nuclear transfer embryos generated by protocols developed for animal eggs, such as for the rhesus monkey, the rabbit, the cow or mice, lead to developmental arrest with human eggs. The Examples below distinguish the inventive methods from what has been attempted by others.

Example 6

Nuclear Transfer Embryos Develop if the Oocyte Genome is not Removed

Figure 2A:
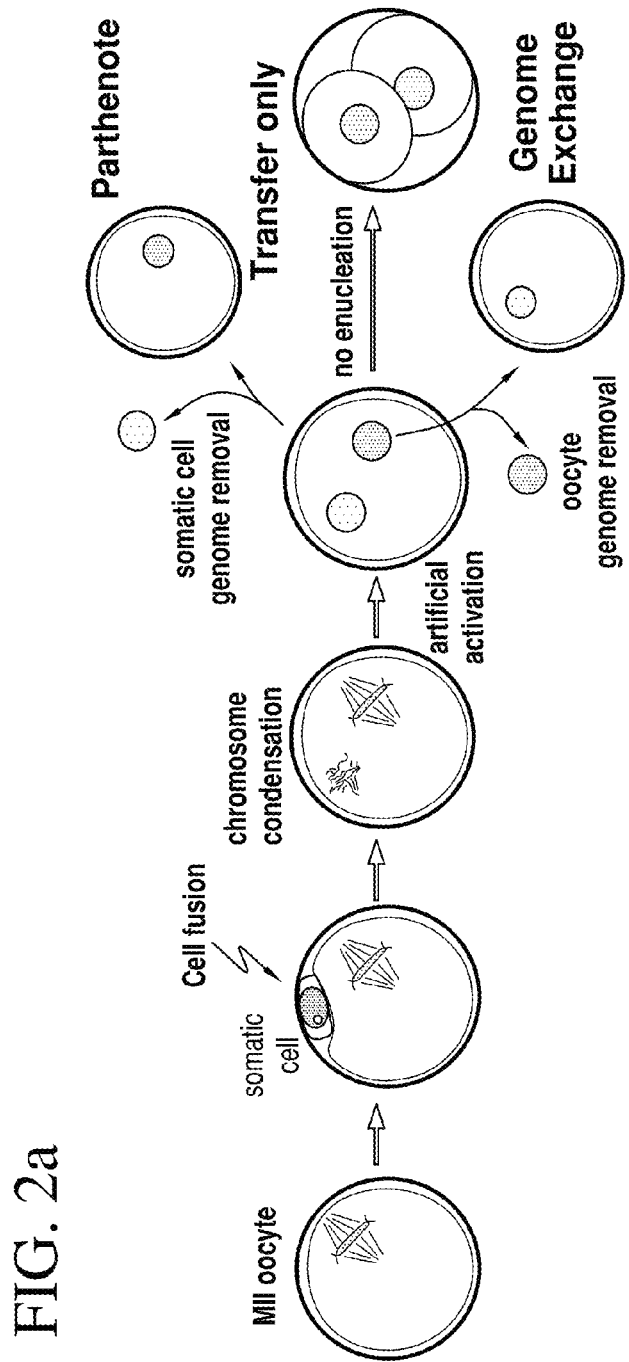
FIGS. 2*a*-2*c* depict development to the blastocyst stage after nuclear transfer without removal of the oocyte genome.
Figure 2B:
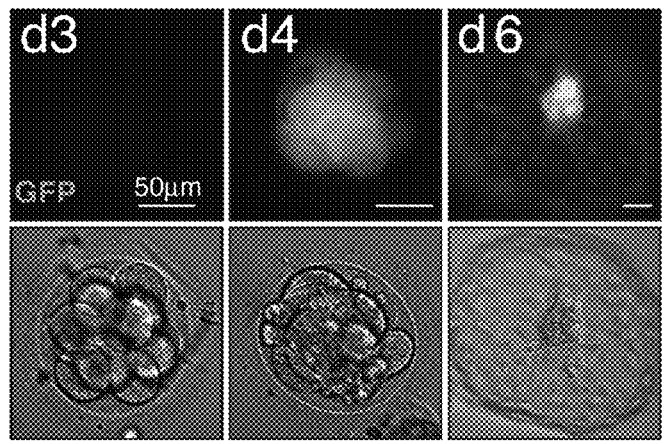
Figure 2C:
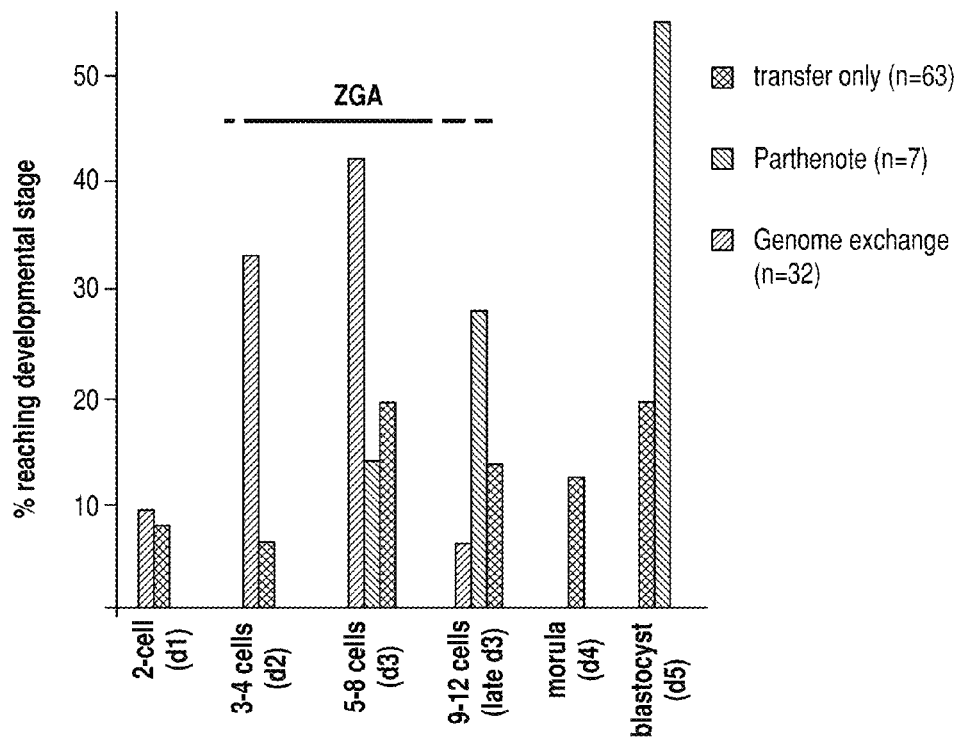

In order to address the question why nuclear transfer embryos did not develop using conventional methods, we developed a new method. Instead of removing the oocyte genome, we left the oocyte genome in the egg, and transferred the somatic cell genome (FIG. 2a). These embryos cleaved, and developed to late cleavage stages by day 3 of development. On day 3, GFP fluorescence was not yet detectable (FIG. 2b). Embryos continued development to the morula stage and initiated expression from the GFP transgene contained in the transferred somatic cell genome. On day 5 and day 6 embryos reached the expanded and hatching blastocyst stages (FIG. 2b). GFP was expressed in all cells of the embryo, suggesting that the somatic cell genome was expressed and accurately segregated during mitoses. Embryos reached the blastocyst stage at least as often as parthenogenetic control embryos (FIG. 2c), suggesting that the somatic cell genome did not negatively interfere with preimplantation development.

To derive embryonic stem cell lines from these blastocysts, the inner cell mass was isolated from 13 blastocysts using laser-assisted micromanipulation. This was done by ablating the trophectoderm with 40-50 laser pulses (Hamilton Thorne Laser system), each 500 µs long.

The inner cell mass was then placed on a feeder layer of gamma-irradiated mouse embryonic fibroblasts. Three stem cell outgrowths were observed 7-14 days post plating, and two of these gave rise to stable embryonic stem cell lines (FIG. 3). These results suggest that there is nothing intrinsically wrong with the somatic cell nucleus, but rather that the removal of the oocyte genome—or components associated with it—precludes preimplantation development of somatic cell nuclear transfer embryos.

Example 7

SOPS Cell Lines Contain A Triploid Genome and Mitochondria of the Oocyte Donor

Figure 3A:
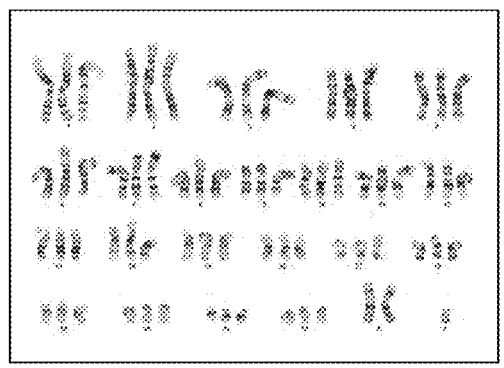
FIGS. 3*a*-3*e* depict derived stem cells and confirms that pluripotent nuclear transfer cell lines can be generated.
Figure 3B:
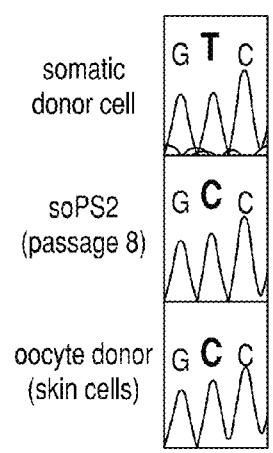

To determine whether the embryonic stem cells contained the somatic cell genome, karyotype analysis was performed. Both embryonic stem cell lines were triploid (FIG. 3a). One of the two cell lines contained an additional chromosome 17 of somatic cell origin. Short tandem repeat analysis showed that the nuclear genome contained a haploid genome of the oocyte and a diploid genome of the skin cell (Table 1). We termed these cells soPS cells, because they are pluripotent stem cells containing the genome of the somatic cell as well as of the oocyte. The mitochondrial genome was of egg donor origin without any sign of heteroplasmy for either cell line (FIG. 3b). Mitochondria transferred with the somatic cell may be lost during preimplantation development or simply outnumbered by the mitochondria of the oocyte. This finding suggests that a somatic cell genome can participate in a normal embryonic mitosis, at least when the oocyte genome is present.

Example 8

Figure 3C:
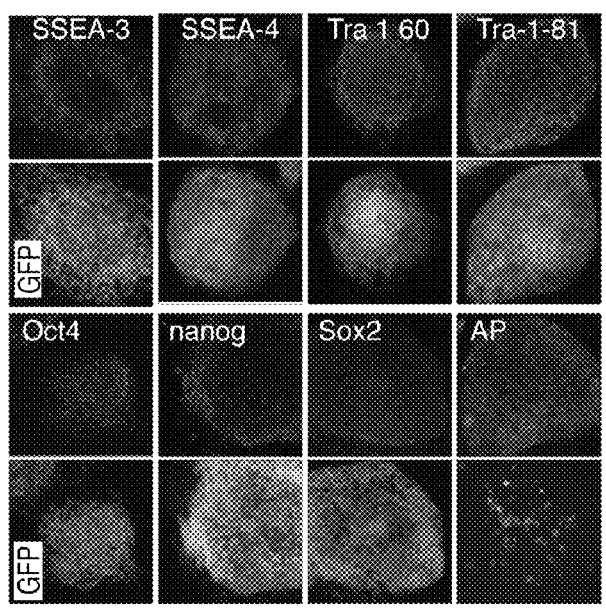
Figure 3D:
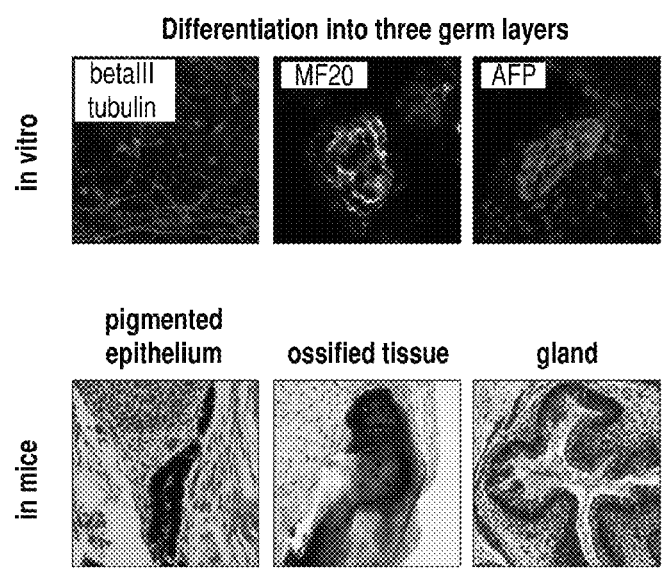
Figure 3E:
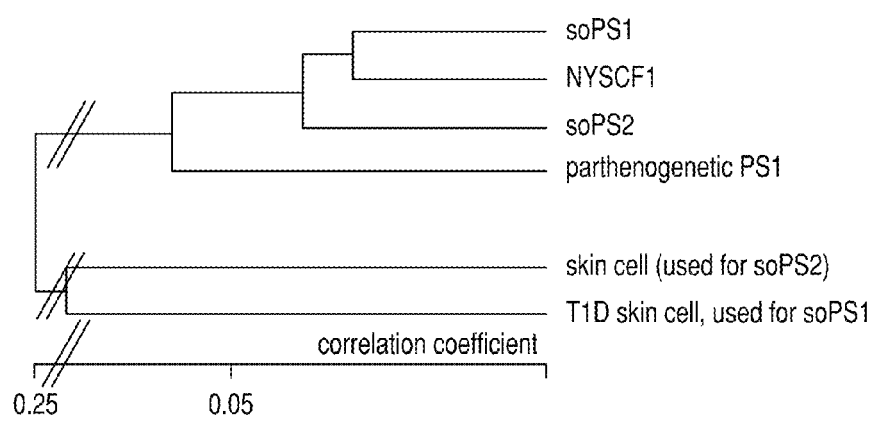

Human Oocytes Reprogram A Somatic Cell to a Pluripotent State soPS embryonic stem cell lines expressed the molecular markers characteristic of pluripotent stem cells, including the pluripotency transcription factors OCT4, NANOG and SOX2, as well as the cell surface markers SSEA3,-4, TRA1-60, and alkaline phosphatase (FIG. 3c). When these cells were differentiated either in vitro in an embryoid body culture, or in vivo after injection into an immuno-compromised mouse, they differentiated spontaneously into cell types of all three germ layers, including retinal pigmented epithelium, bone, cartilage and gland-like structures (FIG. 3d). Gene expression analysis using microarrays were then performed. The transcriptome of nuclear transfer ES cells were compared to other pluripotent cell types. They clustered closely together with a human embryonic stem cell line derived from a fertilized embryo (NYSCF1), and with the parthenogenetic stem cell line pES1 (FIG. 3c). Induced pluripotent stem cells (iPS cells) derived from the same skin cells or from skin cells of the egg donor also clustered with the stem cell lines derived from embryos (FIG. 3e). This result suggests that the oocyte had reprogrammed the somatic cell genome to an embryonic state.

Figure 4A:
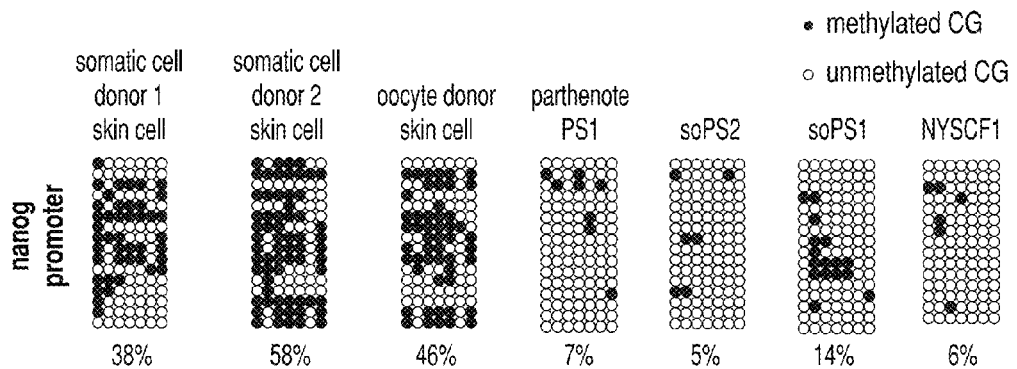
FIGS. 4*a*-4*b* confirm that the somatic cell genome was reprogrammed to an embryonic/pluripotent state.
Figure 4B:
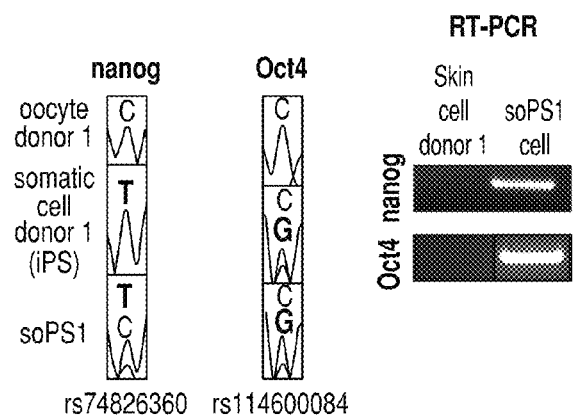

To determine if the somatic cell genome had indeed been reprogrammed, the DNA methylation status of the Nanog promoter that is normally methylated in somatic cells, and demethylated in embryonic stem cells, was examined. High levels of DNA methylation in the somatic cells (58% for the nanog promoter), and very low levels in the nuclear transfer ES cells (5%) (FIG. 4a) were found. Importantly, both the nanog and the Oct4 genes were expressed from the somatic cell genome in soPS cells (FIG. 4b).

It remained possible that the skin cell genome had remained inactive, and that the bulk of gene expression and the ability to differentiate into various cell types were due to the presence of the haploid genome derived from the oocyte donor. To assess allele-specific gene expression single nucleotide polymorphisms (SNPs) were identified that were homozygous in the skin cell, and different from the oocyte donor. For nuclear transfer ESC line 1 (soPS1), 778 expressed SNPs were found and for nuclear transfer soPS2, 483 such SNPs were found. A library containing those SNPs was generated from cDNA of the two soPS cell lines and sequenced to quantify the presence of each allele. The more frequently a particular SNP is detected, the more highly it is expressed.

Figure 5:
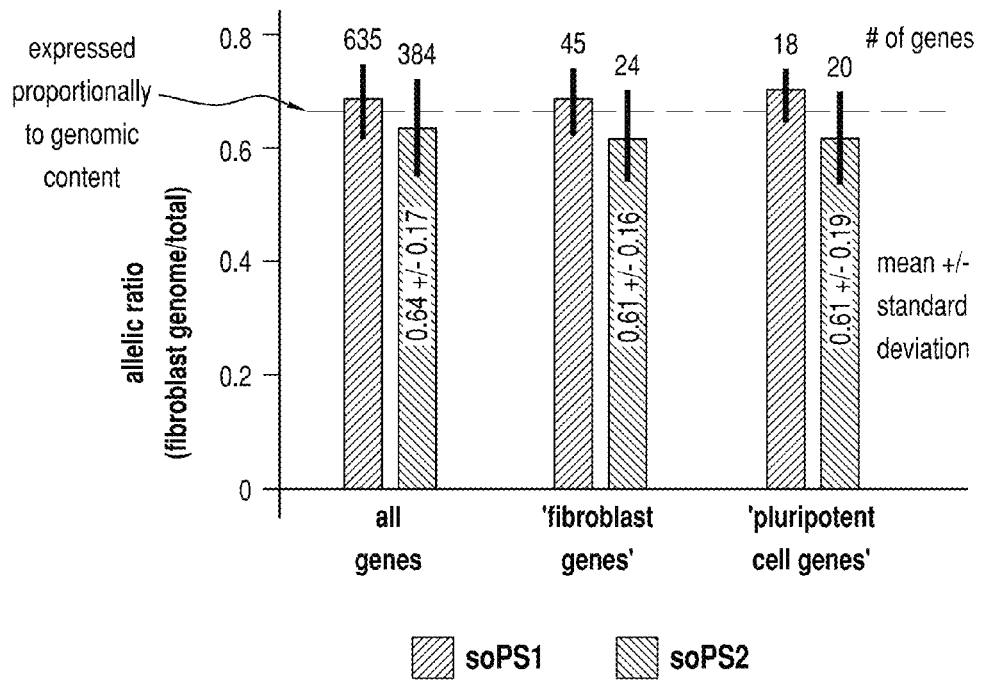
FIG. 5 confirms that the somatic genome has lost the memory of origin. This figure depicts the average allelic ratio of gene expression for three different group of genes: genes preferentially expressed in pluripotent cells, fibroblasts (skin cells) and all genes represented in the RNA expression array and the SNP allelotyping experiment.

When analyzing the relative contribution of the all three genomes in the nuclear transfer cell lines, it was found that, on average, two-thirds originated from the diploid skin cell genome that had been transferred into the oocyte, and one-third originated from the haploid oocyte genome. This demonstrates that the skin cell genome was equally active as the oocyte genome and therefore had been reprogrammed to an embryonic state. We then identified genes that were represented in the microarray experiment described in FIG. 3e, as well as in the SNP sequencing experiment, and found 635 such gens for soPS1, and 384 such genes for soPS2, termed 'all genes' in FIG. 5. We then examined genes that were highly expressed in pluripotent stem cells ('pluripotent cell genes'), and genes that were highly expressed in skin cells ('fibroblast genes'), and found that these different groups of genes were expressed proportionately to their genomic content. On average, two thirds of the cDNAs originated from the reprogrammed skin cell genome, and one third from the oocyte genome. Thus, there was no bias in the expression from the oocyte versus the skin cell genome (FIG. 5). Preferential expression of 'fibroblast genes' from the formerly somatic genome, or preferential expression of 'pluripotency genes' from the oocyte genome would have indicated an incomplete reprogramming or an epigenetic memory. We did not find evidence for such a memory. This demonstrates that skin cell memory has been erased and that the reprogramming of the formerly somatic cell genome was complete.

Example 9

A Method to Generate Parthenogenetics Stem Cells

Figure 6A:
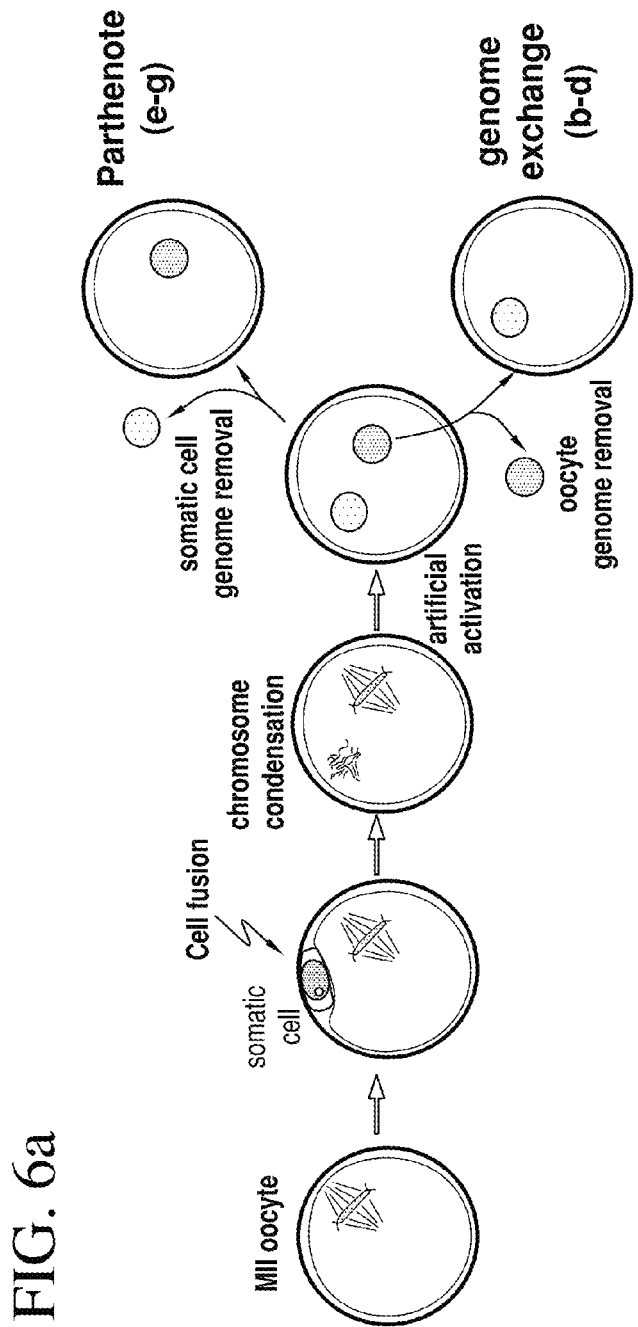

To derive parthenogenetic stem cells and nuclear transfer stem cells with a diploid genome, either the oocyte genome or the somatic cell genome was removed from eggs containing both genomes (FIG. 6a). It was found that after transfer of the GFP labeled donor cell and artificial activation, two interphase nuclei formed (FIG. 6b). The H2B-GFP labelled somatic genome could be readily distinguished from the unlabelled oocyte genome, and either of them could specifically be extracted (FIGS. 6c, 6e). Nuclear transfer embryos containing only the somatic genome regularly developed to cleavage stage embryos containing 4-12 cells, but then invariably arrested without re-activating the GFP transgene (FIG. 6d). In contrast, the parthenogenetic embryos cleaved and developed to the blastocyst stage (FIGS. 6f, 6g). At the blastocyst stage and in parthenogenetic embryonic stem cells, GFP fluorescence was absent (FIG. 6f), suggesting that the somatic cell genome had been removed. It is possible that transfer followed by removal of the somatic cell genome leaves behind the somatic centrosome in the egg, thereby increasing the chance of successful development. the human egg does not contain a centrosome, it is normally introduced by the sperm. the somatic cell would then serve as a centrosome donor instead of the sperm, thereby permitting parthenogenetic development with a centrosome. The inner cell mass was isolated from the parthenogetic embryo by ablating the trophectoderm with repeated laser pulses and then plated on a fibroblast feeder layer.

Figure 7A:
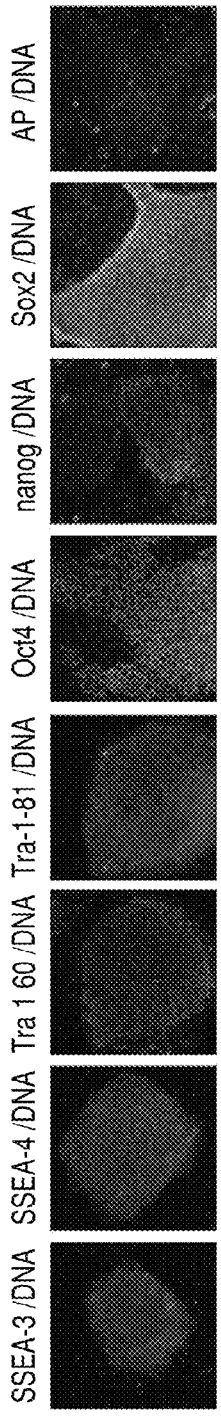
FIGS. 7*a*-7*d* depict the characterization of a parthenogenetic embryonic stem cell line.
Figure 7B:
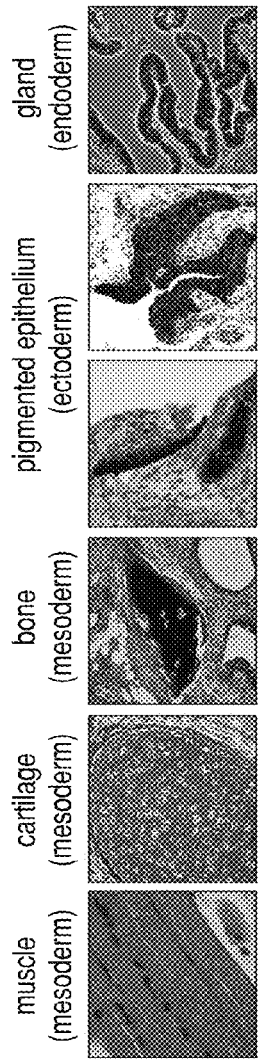
Figure 7C:
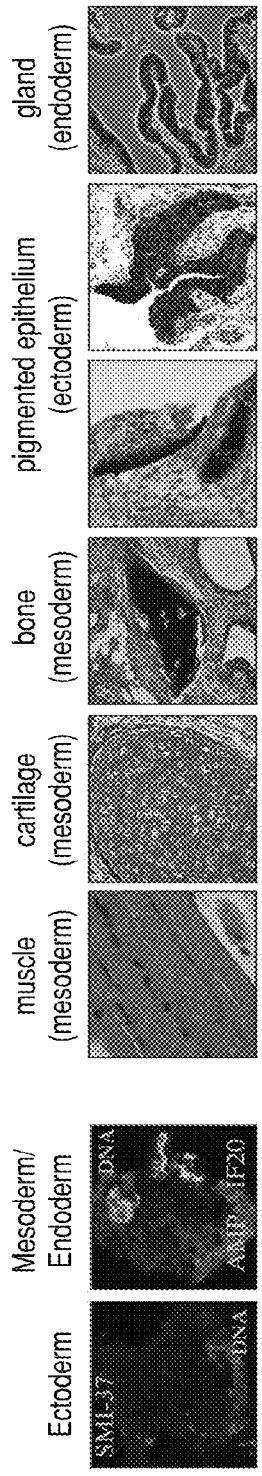
Figure 7D:
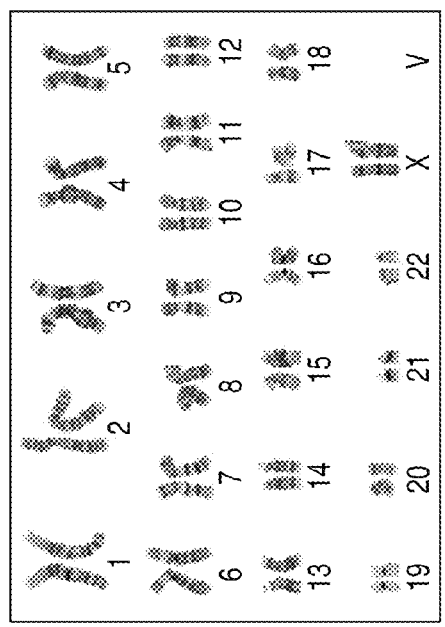

Parthenogenetic ES cells started to grow out after 1-2 weeks, allowing isolation of stable embryonic stem cells (FIG. 6g). Parthenogenetic stem cells that expressed the markers of pluripotency (FIG. 7a), were able to differentiate into cells and tissues of all three germ layers (FIGS. 7b, 7c), and had a female diploid karyotype (FIG. 7d) that was homozygous for the entire genome.

INCORPORATION HEREIN BY REFERENCE

Numerous references are cited herein, all of which are incorporated herein by reference in their entireties.

What is claimed is:

1. A method for producing a human nuclear transfer embryo capable of developing into a triploid blastocyst comprising: transferring a human somatic cell genome into a mature human oocyte by nuclear transfer without removing the genome from the human oocyte and activating the oocyte.

2. The method of claim 1, further comprising allowing the embryo to develop into a blastocyst.

3. The method of claim 2, further comprising isolating an inner cell mass from the blastocyst.

4. The method of claim 3, further comprising contacting the inner cell mass with a human embryonic stem cell medium that comprises Rho kinase inhibitors Y27632 and thiazovivin, for a period of time until an outgrowth of triploid pluripotent stem cells is observed.

* * * * *